US007485149B1

(12) United States Patent
White

(10) Patent No.: US 7,485,149 B1
(45) Date of Patent: Feb. 3, 2009

(54) METHOD AND APPARATUS FOR USE OF A NON-INVASIVE EXPANDABLE IMPLANT

(75) Inventor: John R. White, Winona Lake, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 851 days.

(21) Appl. No.: 10/679,815

(22) Filed: Oct. 6, 2003

(51) Int. Cl.
*A61F 2/28* (2006.01)
(52) U.S. Cl. .................. 623/23.47; 623/23.45; 606/105
(58) Field of Classification Search ... 623/20.14–20.16, 623/20.24–20.25, 20.29, 20.35–20.36, 23.44–23.45, 623/23.47; 606/62–63, 73, 95, 68, 70, 71, 606/105
See application file for complete search history.

(56) References Cited

U.S. PATENT DOCUMENTS

| | | | | |
|---|---|---|---|---|
| 3,869,729 A | * | 3/1975 | Attenborough | 623/20.25 |
| 4,384,373 A | * | 5/1983 | Sivash | 623/23.45 |
| 5,074,882 A | * | 12/1991 | Grammont et al. | 606/63 |
| 5,257,996 A | | 11/1993 | McGuire | |
| 5,323,765 A | | 6/1994 | Brown | |
| 5,326,360 A | * | 7/1994 | Kotz et al. | 623/20.36 |
| 5,330,534 A | | 7/1994 | Herrington et al. | |
| 5,352,230 A | | 10/1994 | Hood | |
| 5,358,524 A | * | 10/1994 | Richelsoph | 623/23.47 |
| 5,370,701 A | | 12/1994 | Finn | |
| 5,382,251 A | | 1/1995 | Hood et al. | |
| 5,391,170 A | | 2/1995 | McGuire et al. | |
| 5,464,407 A | | 11/1995 | McGuire | |
| 5,520,693 A | | 5/1996 | McGuire et al. | |
| 5,626,581 A | | 5/1997 | Staehlin et al. | |
| 5,658,289 A | | 8/1997 | Boucher et al. | |
| 5,704,938 A | | 1/1998 | Staehlin et al. | |
| 5,704,939 A | * | 1/1998 | Justin | 606/63 |
| 5,782,922 A | | 7/1998 | Vandewalle | |
| 5,885,298 A | | 3/1999 | Herrington et al. | |
| 5,997,543 A | | 12/1999 | Truscott | |
| 6,056,755 A | * | 5/2000 | Horas et al. | 606/86 |
| 6,106,525 A | | 8/2000 | Sachse | |
| 6,197,065 B1 | | 3/2001 | Martin et al. | |
| 6,200,317 B1 | | 3/2001 | Aalsma et al. | |
| 6,245,075 B1 | | 6/2001 | Betz et al. | |
| 6,336,929 B1 | | 1/2002 | Justin | |
| 6,383,185 B1 | | 5/2002 | Baumgart | |

(Continued)

FOREIGN PATENT DOCUMENTS

WO  WO 01/78614 A1 * 10/2001

*Primary Examiner*—Corrine McDermott
*Assistant Examiner*—Christopher D Prone
(74) *Attorney, Agent, or Firm*—Harness, Dickey & Pierce, P.L.C.

(57) ABSTRACT

The present invention relates to a non-invasive expandable implant utilizing energy from an epiphyseal growth plate of a human long bone to expand the implant. A bone replacement section includes a housing, an expansion shaft, a connection system, and an implant member. An anchoring member is secured to the second bone portion and spaced from the implant member. The expansion shaft is configured to translate a first distance between the housing and the first bone member. Growth of the bone causes an increase of a second distance between an implant portion and the anchoring member. The increase of the second distance causes the anchoring member to exert a force on a connection system causing an increase of the first distance, thus expanding the implant.

28 Claims, 5 Drawing Sheets

U.S. PATENT DOCUMENTS 6,508,841 B2    1/2003  Martin et al.
6,569,203 B1 *  5/2003  Keller .................... 623/23.47
2002/0151978 A1 * 10/2002 Zacouto et al. .......... 623/17.12
2004/0172138 A1 *  9/2004 May et al. ................ 623/20.36

* cited by examiner

METHOD AND APPARATUS FOR USE OF A NON-INVASIVE EXPANDABLE IMPLANT

FIELD OF THE INVENTION

The present invention relates to a non-invasive expandable implant and more particularly to a non-invasive expandable implant utilizing the energy from the epiphyseal growth plate of a human long bone to expand the implant.

BACKGROUND OF THE INVENTION

From early in fetal life to possibly beyond the teenage years, human bones continue to ossify or grow. Depending on the architecture of a bone, ossification occurs at various locations on the bone and at various times during the maturation of the bone. A femur, for example, may ossify from five different centers. Furthermore, an epiphysis or a location of bone growth of a distal femoral extremity may not unite with the bone, thus finishing the bone growth, until or beyond an age of twenty-years old. Unfortunately, myriad medical conditions may require removal of a distal femoral extremity or other portions of the bone resulting in possible removal of an epiphysis or a growth plate. Patients that require such a medical procedure require a device to maintain the proper length of the bone due to the loss of the growth plate.

Prior implementation of expandable implants required constant monitoring of bone growth and further may have required invasive techniques to affect expansion of the implant. Monitoring bone growth requires repeated interaction with the patient and continual analysis of the bone growth rate and amount. While necessary, constant monitoring may be inconvenient. In addition, the expandable implant requires a certain rate of expansion to maintain the length of the implant approximately equal to other bones and this expansion may require invasive techniques. In lieu, of invasive techniques, portions of the expandable implant may remain accessible for external adjustment. Other possibilities for expansion include exterior devices to affect the change in extension length. Such examples of exterior devices include remote control electrical power extension or magnetic effectuation of expansion.

Remote expanding devices or adjustments with external portions of the expandable implants present myriad difficulties. The chance of infection remains possible with maintenance of any opening into the body in a situation where a portion of implant is externally accessible. When remote devices are used, the possibility exists for inopportune or unwanted expansion of the implant. In addition, the possibility exists that the ability to remotely expand the implant will be completely lost. As such, there remains a need in the art for a non-invasive expandable implant that does not require remote effectuation of expansion. In addition, there is a need in the art for the rate of expansion of the expandable implant to match the corresponding bones for example the left or right femur.

SUMMARY OF THE INVENTION

In accordance with the teachings of the present invention, a non-invasive expandable bone device is implanted in a first bone portion and a second bone portion of a patient to elongate the first bone portion by using growth of the second bone portion. A bone replacement section includes a housing, an expansion shaft, a connection system, and an implant member. An anchoring member is secured to the second bone portion and spaced from the implant member. The expansion shaft is configured to translate within the housing a first distance and is configured to connect to the first bone portion. The first distance may be defined as a distance between the housing and the first bone member. The connection system is attached to the anchoring member and the expansion shaft. The implant portion is configured to be secured to at least a portion of the second bone portion and includes a hollow portion through which the connection system passes. Growth of the bone causes an increase of a second distance; the second distance may be defined as a distance between the implant portion and the anchoring member. The increase of the second distance causes the anchoring member to exert a force on the connection system causing an increase of the first distance, which is due to the expansion of the implant.

Further areas of applicability of the present invention will become apparent from the detailed description, the drawings, and the appended claims provided hereinafter. It should be understood that the detailed description and specific examples, while indicating embodiments of the invention, are intended for purposes of illustration only and are not intended to limit the scope of the invention.

BRIEF DESCRIPTION OF THE DRAWINGS

The present invention will become more fully understood from the detailed description, the appended claims, and the accompanying drawings, wherein:

DETAILED DESCRIPTION OF THE PRESENT EMBODIMENTS

The following description of the present embodiments concerning a method and apparatus for use of a non-invasive expandable implant is merely exemplary in nature and is not intended to limit the invention, its application, or uses. Moreover, while the present invention is generally described in detail below with respect to a distal femoral replacement, a prosthetic knee joint, and a resurfacing tibial component, it will be appreciated by those skilled in the art that the present invention is not limited only to the knee joint and may be applied to various other long bones and joints of the human body such as but not limited to the tibia, fibula, humerus, ulna, and radius. It will also be appreciated by those skilled in the art that inclusion of a joint, such that present invention utilizes two or more bones connected by joint, is merely an embodiment of the present invention and no such limitation exists. As such, the present invention may be configured for use in one or more bones but may or may not span a joint. To that end, the present invention may be configured to utilize the energy of a growth plate of a single long bone to effectuate the extension of the implantable device in a non-invasive manner.

Figure 1:
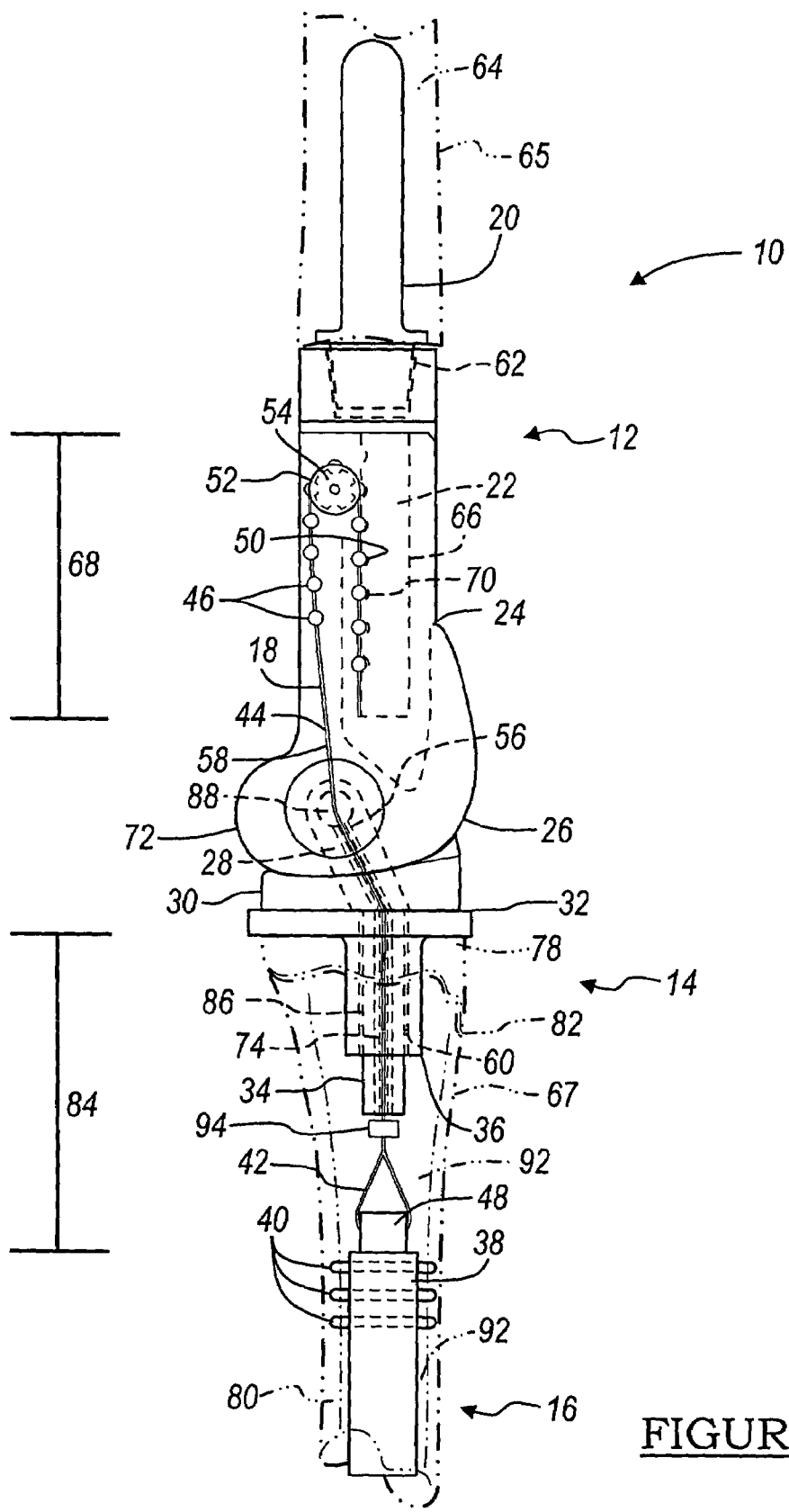
FIG. 1 is a side view of the non-invasive expandable implant constructed in accordance with the teachings of the present invention.

Referring to FIG. 1, there is shown a non-invasive expandable implant generally indicated by reference numeral 10. The expandable implant 10 includes a femoral section 12, a tibial section 14, and an anchoring member 16. The non-invasive expandable implant 10 further includes a connection system 18 that travels between the femoral section 12 through the tibial section 14 and then attaches to the anchoring member 16. The femoral section 12 further includes a modular intramedullary stem 20 that may be connected to an expansion shaft 22. The expansion shaft 22 is disposed within a housing 24 and when expanded translates out of the housing 24, thus pushing on the intramedullary stem 20. The housing 24 further defines a prosthetic condylar region 26, which is configured to articulate in a similar fashion to portions of a natural knee (not shown).

The tibial section 14, which may be partially contained within a second bone member or portion 67, further includes a yoke 28 that is connected to a bearing component 30. The bearing component 30 is connected to a tibial tray 32 and able to partially rotate about the tibial tray 32. A yoke stem 34, which is attached to the yoke 28, is disposed within a tibial stem 36 and passes through the bearing component 30 and the tibial tray 32.

The anchoring member 16 includes an anchor plug 38, which is attached by fasteners 40. The fasteners 40 may at least include but are not limited to bone screws, straight pins, bone cement, or combinations and derivations thereof. A connection system attachment point 42 may be configured as the location where the anchor plug 38 attaches to the connection system 18. The anchor plug 38 may be attached at various suitable locations within a tibial intramedullary canal 92. It should be appreciated that the anchor plug 38 may be used with the fasteners 40 or other such devices that provide an anchor within the intramedullary canal of a bone. One such exemplary device that includes a threaded anchor plug is disclosed in commonly assigned U.S. Pat. No. 6,508,841, which is hereby incorporated by reference as if fully set forth herein.

The connection system 18 further includes a cable 44, to which a plurality of projections 46 is attached. The cable 44 further defines an anchoring member connection 48 and an expansion shaft attachment point 50. The cable 44 is configured to travel over a pulley 52, which may include a ratchet mechanism 54. The cable 44 may further travel through a yoke channel 56 from a femoral section channel 58 to a yoke stem channel 74; all of which are shown in greater detail in FIG. 4. The yoke channel 56, the femoral section channel 58, and the yoke stem channel 74 are all configured to not apply additional tension to the connection system 18 when the implant 10 articulates through various positions as explained in greater detail below.

The modular intramedullary stem 20 is connected to the expansion shaft 22 using a Morse taper junction 62. In the present embodiment the Morse taper junction 62 is a self-locking taper junction. The Morse taper junction 62 provides a secure junction without the use of additional fasteners. The Morse taper junction 62, however, may be reinforced or substituted with mechanical fasteners (not shown) or other forms of connection (not shown).

The modular intramedullary stem 20 is placed in the bone during surgery that may include complete removal of the distal femoral extremity. The intramedullary stem 20 is configured to be secured in a femoral intramedullary canal 64 with a press fit or a friction fit. As such, the intramedullary stem 20 may be sized to various dimensions of the femoral intramedullary canal 64. It will be appreciated that the expansion shaft 22 may be connected to the femur or any such bone with many types of connections. Connecting the expansion shaft 22 to the bone with or without the use of the intramedullary stem 20, therefore, remains within the scope of the present invention.

Variation in the dimensions of the femoral intramedullary canal 64 may necessitate modularity of the intramedullary stem 20. As such, the modular intramedullary stem 20 may be sized for various patients. Notwithstanding that the intramedullary stem 20 is fabricated in many suitable sizes, each of the intramedullary stems 20 are configured to secure to the expansion shaft 22.

Figure 2A:
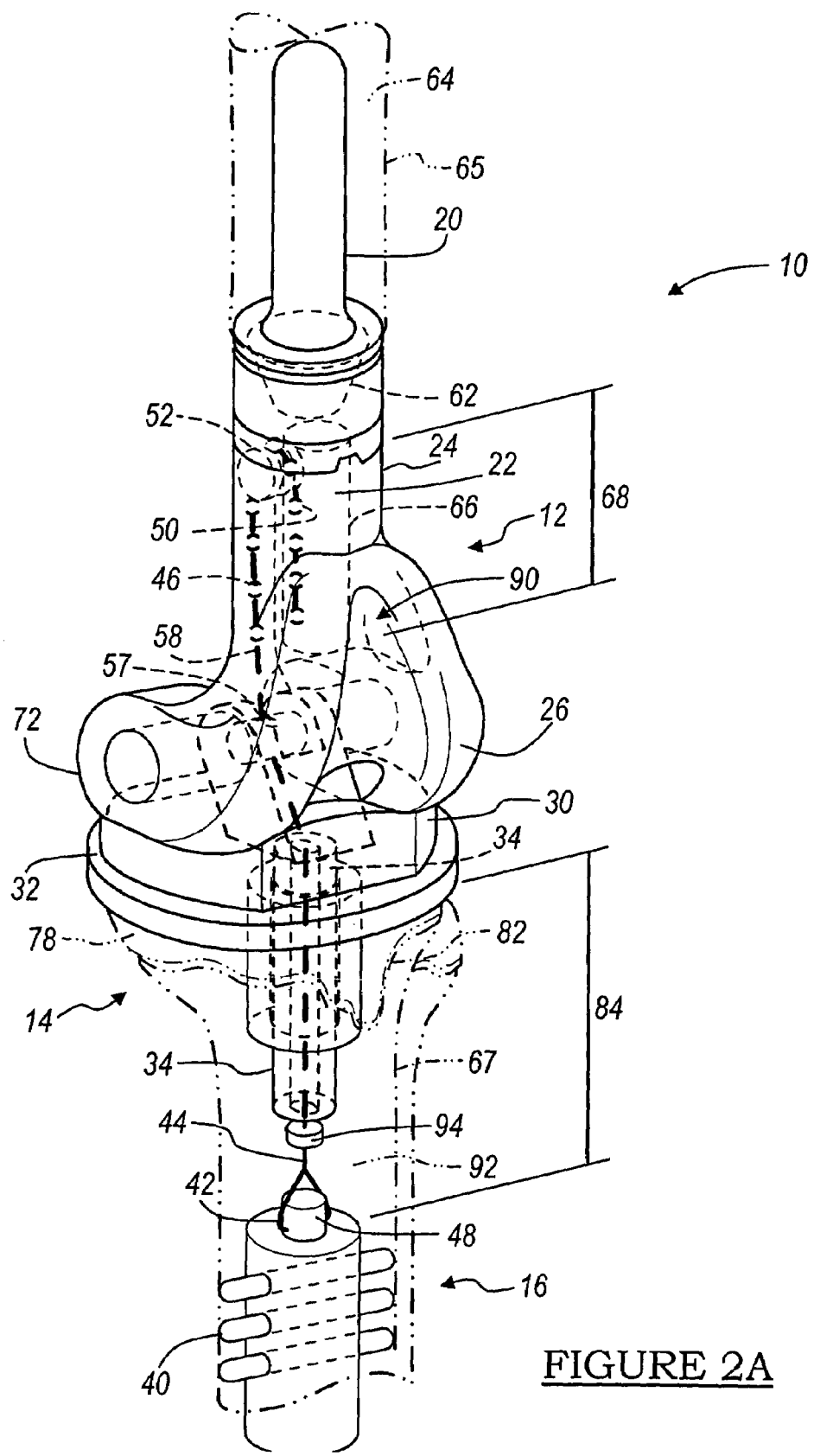
FIG. 2A is perspective view of the implant of FIG. 1, shown in an extension condition.
Figure 2B:
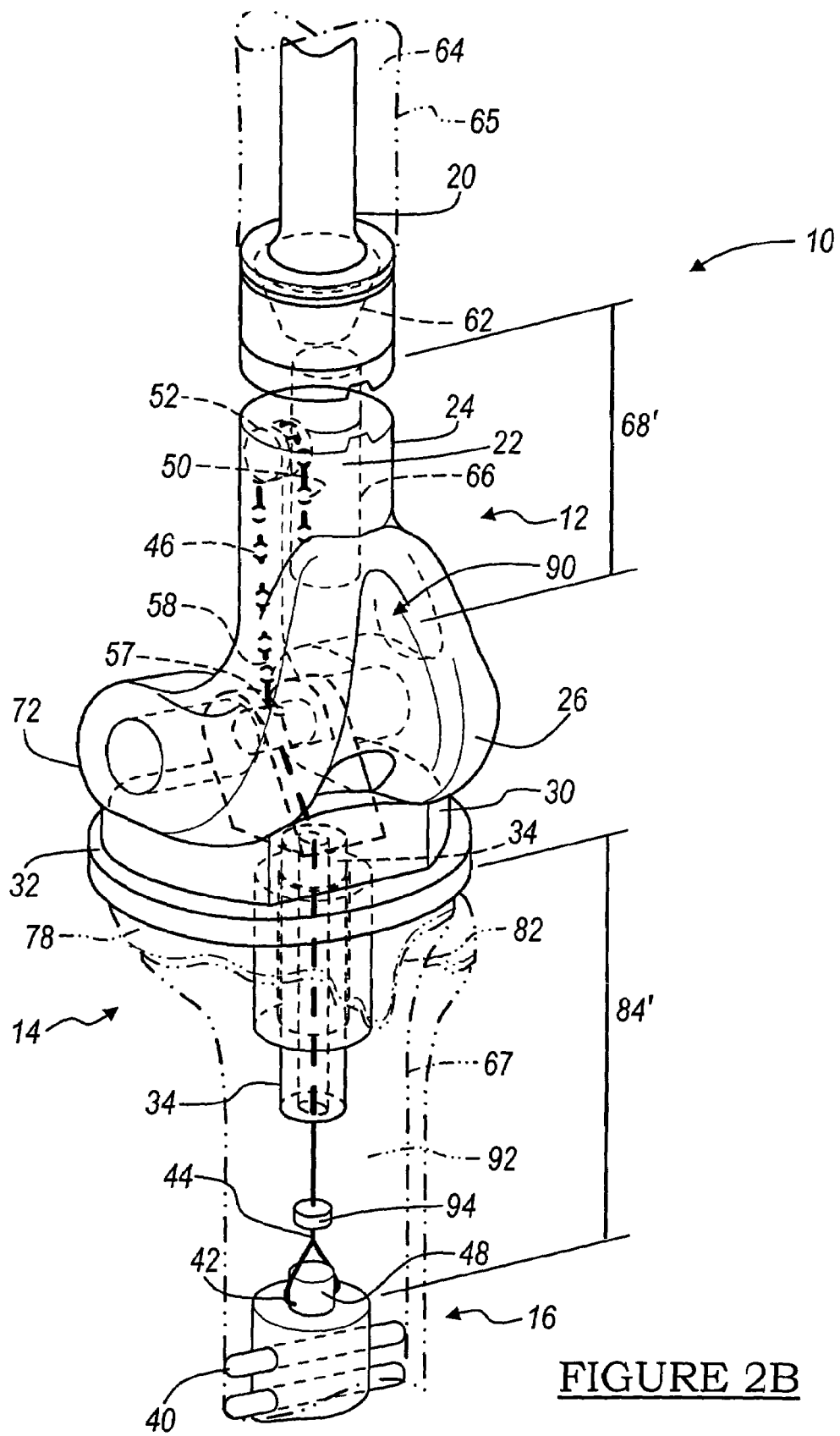
FIG. 2B is perspective view of the implant of FIG. 2A, showing expansion of the implant.

The expansion shaft 22 is configured to translate within a femoral section sleeve 66 in response to a force exerted by the connection system 18. Translation of the expansion shaft 22 causes an increase in a first distance 68 between the housing 24 and the expansion shaft 22. The rate of the increase in the first distance 68 generally mimics natural growth of the bone that the expandable implant 10 has replaced. It will be appreciated that an increase of the first distance 68 is noted as a first distance 68', as shown in FIG. 2B.

Indentations 70 of the expansion shaft 22 are configured to mesh with the projections 46 of the cable 44. The expansion shaft 22 is configured so that at least three of the projections 46 need to be meshed with at least three of the indentations 70 of the expansion shaft 22 to provide enough force to move the expansion shaft 22 and thus increase the first distance 68. In the present invention the projections 46 are configured as modified spherical balls spaced apart and attached to the cable 44. As such, the indentations 70 are configured to accept the spherical balls. It will be appreciated that other configurations are available to mesh the cable 44 with the expansion shaft 22. It should also be appreciated that the cable 44 may be substituted with other modified connection devices.

The housing 24 is configured to articulate similar to the distal femoral extremity that the expandable implant 10 has now replaced. To that end, the housing 24 is further configured to resemble the typical components of a healthy knee (not shown). The housing 24, therefore, includes the prosthetic condylar region 26 that is configured to articulate about the bearing component 30. As such, the housing 24 and the bearing component 30 are configured to mimic the movement of the natural knee (not shown) but are modified to the extent that such modifications and deviations from the natural knee provide the requisite stability required by the patient.

It will be appreciated that a knee joint 72 of the present invention is configured with more restraint than a natural knee (not shown), such that a natural knee may have a greater range of motion than the knee joint 72. The constraint of motion provides additional stability for a patient but inherently restricts otherwise natural movement. The expandable implant 10 is, therefore, configured to constrain the knee joint 72 as a benefit to the patient after surgery and during use of the present invention. It is envisioned, however, that after the patient's bones have sustained full growth, such that the epiphyses have united with the bone, the expandable implant 10 is then removed and replaced with a non-expanding prosthetic knee joint. To that end, one such exemplary knee joint, which may replace the present invention after full bone growth, is disclosed in U.S. Pat. No. 6,165,223, which is hereby incorporated by reference in its entirety as if fully set forth herein.

The knee joint 72 of the present invention may be a modified hinge joint, wherein such modifications include configuring the knee joint 72 so that it connects with the housing 24 and the tibial section 14. As such, the knee joint includes a modified rotating/sliding constrained prosthetic knee as disclosed in U.S. Pat. No. 5,370,701, which is hereby incorporated by reference in its entirety as if fully set forth herein.

One such modification of the knee joint 72 is the yoke channel 56 and the yoke stem channel 74, both of which allow the cable 44 of the connection system 18 to pass from the expansion shaft 22 to the anchoring member 16. The yoke channel 56 and the yoke stem channel 74 are additionally configured to prevent unwanted tensioning of the cable 44 due to flexion and extension of the knee joint; such that, unwanted tension may cause unwanted expansion of the of the expandable implant 10.

The yoke 28 and the yoke channel 56 are further configured so that a rod 55, which holds the knee joint 72 together, includes a yoke channel entrance point 57. The yoke channel entrance point 57 may be oversized to accommodate the cable 44 as it passes through the knee joint 72. The entrance point 57 may be configured so that the knee joint 72 so that the knee joint 72 does not apply any additional tension to the cable 44 while the knee joint 72 is in a flexion condition 96, an extension condition 98, and a plurality of positions in between the flexion condition 96 (shown in FIG. 3) and the extension condition 98 (shown in FIGS. 1, 2A, and 2B). It will be appreciated that the knee joint 72 may be held together by connections other than the rod 55, such as a snap-fit or a connection with a bearing pack.

As such, the connection system 18 may be configured to pass through the center of rotation of the knee joint 72 to prevent application of additional tension to the connection system 18 as mentioned above. Furthermore, the path through which the connection system 18 passes is configured to not change length when the knee is in extension, flexion, or positions therebetween. It should be appreciated, therefore, that the non-invasive expandable implant 10 may be configured so that when the implant 10 is in extension or flexion, no forces are imparted on the implant 10 that would cause expansion of the implant 10 other than the force imparted on the implant 10 due to the anchor plug 38 contained within the growing bone.

The tibial section 14 includes the bearing component 30 upon which the prosthetic condylar region 26 articulates. The bearing component 30 defines an aperture 76 (FIG. 4) through which the yoke stem 34 passes. It will be appreciated that the bearing component 30 may be configured to supply similar functionality of the medial and lateral menisci. To that end, the bearing component 30 may be fabricated from an ultra high molecular weight (UHMW) polyethylene. Those skilled in the art will readily appreciate that the bearing component 30 may be fabricated from any suitable biocompatible material that is able to withstand regime into which it is implanted.

The bearing component 30 is configured to attach to the tibial tray 32. The tibial tray 32 is configured to be implanted in a modified proximal tibial plateau 78 and positioned in a tibia 80 superior to a proximal tibial epiphyseal growth plate 82. The position of the tibial tray 32 is such that the growth of the growth plate 82 causes an increase in a second distance 84 between the anchoring member 16 and the tibial tray 32. Furthermore, the aperture 76 continues through the tibial tray 32 and into the tibial stem 36 and is, thus, configured to allow the yoke stem 34 to be disposed within the tibial stem sleeve 60. It will be appreciated that the tibial section 14 is not limited to an installation within the tibia 80 but may be installed into any growing second bone portion 67.

The tibial tray 32 is connected to the tibial stem 36. The tibial stem 36 is configured to be implanted in the modified proximal tibial plateau 78 but is further configured to move in response to growth from the growth plate 82. As the growth plate 82 grows, the tibial stem 36 and the tibial tray 32 moves away from the anchoring member 16, resulting in an increase of the second distance 84. It should be noted that an increase in the second distance 84 is in indicated as a second distance 84', as shown in FIG. 2B.

It will be appreciated by those skilled in the art that the tibial tray 32 may be configured to attach to the modified proximal tibial plateau 78 so that when the tibial growth plate 82 grows, thus increasing the length of the tibia 80, the second distance 84 increases to the second distance 84'. As such, the second distance 84 is generally between the tibial tray 32 and the anchoring member 16. Furthermore, the tibial tray 32 may be fabricated from various bio-compatible materials to promote bone growth to further fasten the tibial tray 32 to the modified proximal tibial plateau 78.

Figure 4:
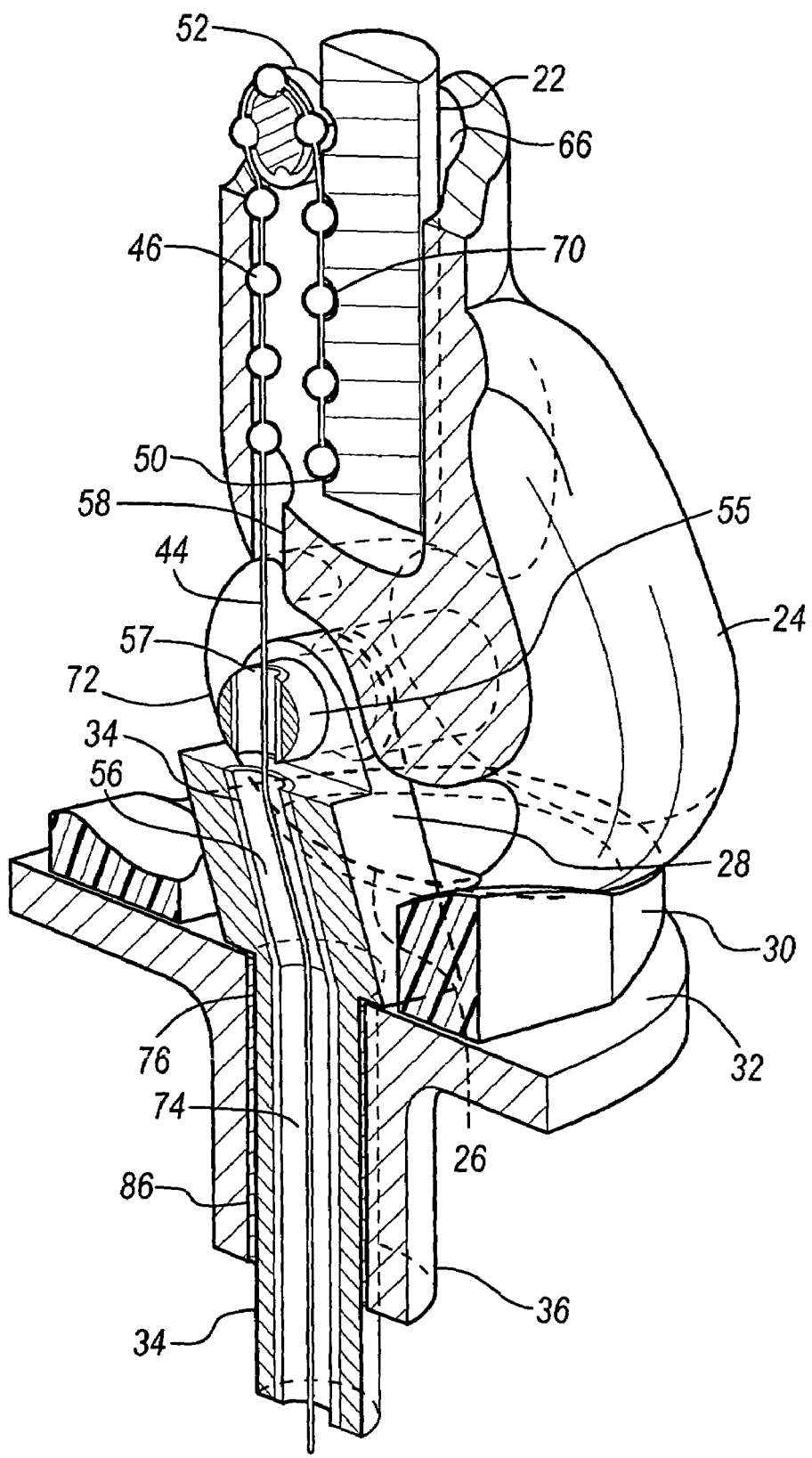
FIG. 4 is a perspective view of the implant of FIG. 1 showing a more detailed path of a connection system through a knee joint of the present invention.

The tibial stem 36 further includes the tibial stem sleeve 60 and a cylindrical bushing 86, shown in greater detail in FIG. 4. The tibial stem sleeve 60 and the cylindrical busing 86 are configured to accept the yoke stem 34 and permit the yoke stem 34 to rotate and translate within the tibial stem sleeve 60. Rotation and translation of the yoke stem 34 in the tibial stem sleeve 60 permits movement within the tibial section 14 to alleviate transmission of stress to other portions of the expandable implant 10.

Figure 3:
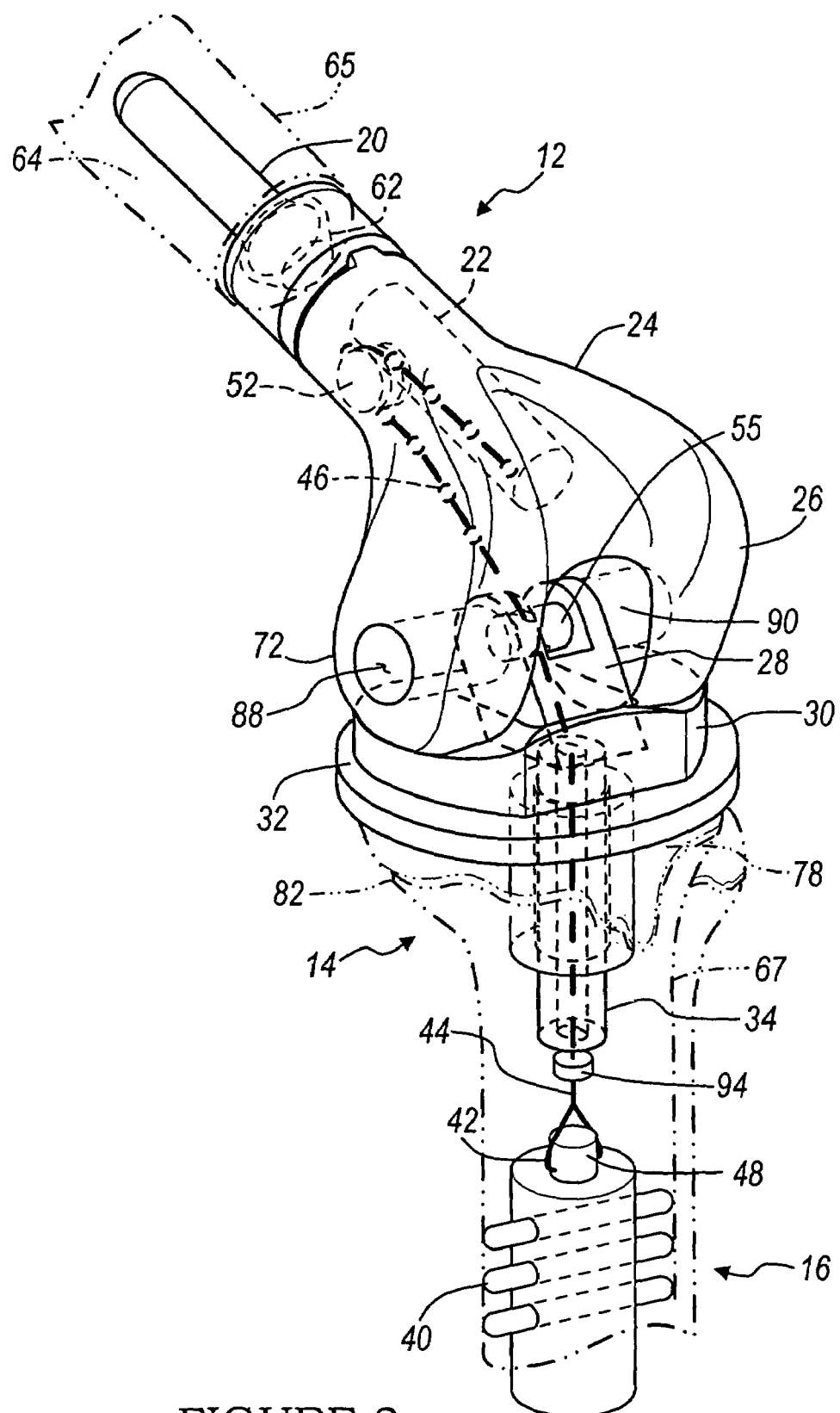
FIG. 3 is a perspective view of the implant in FIG. 1 shown in a flexion condition.

The yoke 28 may be configured to attach to a rotating hinge 88 with the rod 55 through an intercondylar notch 90, which is shown in greater detail in FIG. 3. The yoke 28 further includes the yoke channel 56 which continues through to the yoke stem channel 74 of the yoke 28, as shown in FIG. 4. The yoke channel 56 and the yoke stem channel 74 are configured to permit the cable 44 of the connection system 18 to pass from where it meshes with the expansion shaft 22 to where it connects with the anchoring member 16. As mentioned earlier, the rotating hinge 88 and various components of the implant 10 are configured to not apply additional tension to the cable 44 during the extension condition 98 of the knee joint 72 and the flexion condition 96, which is defined by posterior bending of the limb as illustrated in FIG. 3.

The anchoring member 16 includes the anchor plug 38 and the fasteners 40. The anchor plug 38 is secured in the tibial intramedullary canal 92 and spaced inferior to the tibial section 14. The anchor plug 38 may be secured to the tibial intramedullary canal 92 by use of mechanical threads (not shown) or the fasteners 40. The fasteners 40 may be conventional bone screws. One skilled in the art will readily appreciate that fixation of the anchor plug 38 may use mechanical, chemical, or biomechanical fastening and, as such, may take many suitable forms such as mechanical threads, a porous exterior to promote bone growth, or bone cement. Such methods may require modular sizing of the anchor plug 38 to accommodate various sizes of the tibial intramedullary canal 92. Notwithstanding the modularity of the anchor plug 38, the methods of fastening may be combined to further facilitate successful fixation of the anchor plug 38 in the tibial intramedullary canal 92.

The anchor plug 38 further includes the anchoring member connection 48 that is configured to connect the cable 44 to the anchor plug. A modified crimp 94 may be used to secure the cable 44 to the anchor plug 38, but one skilled in the art will readily appreciate that many methods exist to connect the cable 44 to the anchor plug 38.

The connection system 18 includes the cable 44 having a path throughout the implant 10. The connection system 18 connects to the expansion shaft 22 with the plurality of the projections 46. From the expansion shaft 22, the cable 44 follows a path over the pulley 52, which may include the ratchet mechanism 54. From the pulley 52, the cable 44 travels through the femoral section channel 58 and then passes through the knee joint 72. From the rod 55 of the knee joint 72, the cable continues through the yoke channel 56 and the yoke stem channel 74. After passing through the yoke stem channel 74, the cable 44 continues through the tibial intramedullary canal 92 and connects with the anchor plug 38 at the connection system connection point 42.

The connection system 18 is, therefore, configured to transmit a force from the anchoring member 16 to the expansion shaft 22. The force is initiated by the second distance 84 increasing between the tibial section 14 and the anchoring member 16 to at least the second distance 84' due to growth of the proximal tibial growth plate 82. The force is transmitted through the cable 44 to the expansion shaft 22, where the projections 46 of the cable 44 mesh with the indentations 70 of the expansion shaft 22. The expansion shaft 22 then translates in response to the force applied by the cable 44 and the anchoring member 16. The translation results in the first distance 68 between the housing 24 and the expansion shaft 22 increasing. To that end, an increase in the first distance 68 is indicated in FIG. 2B as the first distance 68'.

It should be appreciated that the implant 10 is configured so that only the force generated by the growth of the growth plate 82 provides the force through the cable 44 to expand the expansion shaft 22, ultimately expanding the implant 10. The implant 10, therefore, is configured so that flexion, extension, and all other types of articulation of the implant 10 do not impart additional forces on the cable 44. It follows, therefore, expansion of the implant 10 is exclusively linked to the growth of the growth plate 82.

The connection system 18 may be further configured with the ratchet mechanism 54. The ratchet mechanism 54 may introduce a modified conventional ratchet to prevent collapse of the expansion shaft 22 during expansion. It will be appreciated that many other devices can be configured to provide anti-collapse functionality. It will be further appreciated that the ratchet mechanism 54 may be introduced into various portions of the implant 10, such as integral to the expansion shaft 22 or any location to provide anti-collapse functionality. It will be additionally appreciated that multiple ratchet mechanisms may be introduced into the implant 10.

The expandable implant 10 is configured such that increases in the first distance 68 and the second distance 84 are similar; such that, expansion of the implant 10 approximates natural bone growth. To that end, the proximal tibial growth plate 82 growth rate is similar to that of the distal femoral growth plate (not shown), which has been replaced by the expandable implant 10. As such, the expandable implant 10 may utilize the energy and similar growth rate of the proximal tibial growth plate 82 to power the expandable implant 10 to generally recreate the natural growth rate of the proximal femoral growth plate (not shown).

One skilled in art will readily appreciate that the connection system 18 may be further configured to adjust expansion rates of the expandable implant 10 to different desired expansion rates by adding modified conventional gearing to the connection system 18. As such, a desired growth rate can be achieved even when the expandable implant 10 is secured within a single bone having differing epiphyseal growth rates. Implantation in a single bone necessarily introduces dissimilar growth plate growth rates, which necessitates the aforementioned conventional gearing to maintain the desired expansion rate.

The many components of the expandable implant 10 may be fabricated from any suitable biocompatible material that would survive the regime into which the expandable implant is introduced. Exemplary materials such as a titanium alloy like Titanium 6 Aluminum 4 Vanadium (Ti-6Al-4V or Ti64) or Cobalt Chrome Molybdenum may be used. It will be appreciated that Ti64 is more biocompatible than Cobalt Chrome Molybdenum, but Cobalt Chrome Molybdenum exhibits better wear characteristics. As such, both metals, suitable biocompatible material, or combinations and derivations thereof may be used where appropriate.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A non-invasive expandable bone device adapted to be in a first bone portion of a patient that is capable of using growth of a second bone portion to elongate the first bone portion, the device comprising:
    a bone replacement configured to be secured to the first bone portion;
    an anchoring member configured to be secured to the second bone portion; and
    a connection system including a cable that connects said bone replacement to said anchoring member, wherein said connection system is configured to expand said bone replacement in response to a force exerted by said anchoring member due to the growth of the second bone portion,
    wherein said bone replacement includes an articulable joint that connects the first bone portion to the second bone portion.

2. The device of claim 1, wherein a first bone includes the first bone portion and the second bone portion.

3. The device of claim 1, wherein said bone replacement includes an expansion shaft that is configured to translate within a housing and is adapted to connect to the first bone portion.

4. The device of claim 3, wherein said expansion shaft translates in said housing a first distance and the second bone portion grows a second distance.

5. The device of claim 1, wherein said bone replacement is configured to prevent an additional application of force on said connection system when said joint is in one of a flexion condition, an extension condition, and a plurality of positions between said flexion condition and said extension condition.

6. A non-invasive expandable bone device adapted to be in a first bone portion of a patient that is capable of using growth of a second bone portion to elongate the first bone portion, the device comprising:
    a bone replacement configured to be secured to the first bone portion;
    an anchoring member configured to be secured to the second bone portion; and
    a connection system including a flexible connector that connects said bone replacement to said anchoring member, wherein said connection system is configured to expand said bone replacement in response to a force exerted by said anchoring member due to the growth of the second bone portion,
    wherein said bone replacement includes an expansion shaft that is configured to translate within a housing and is adapted to connect to the first bone portion,
    wherein said expansion shaft translates in said housing a first distance and the second bone portion grows a second distance, and
    wherein a first increase in said first distance is caused by a second increase in said second distance.

7. A non-invasive expandable bone device adapted to be in a first bone portion of a patient that is capable of using growth of a second bone portion to elongate the first bone portion, the device comprising:
    a bone replacement configured to be secured to the first bone portion;

an anchoring member configured to be secured to the second bone portion;
a connection system including a flexible connector that connects said bone replacement to said anchoring member, wherein said connection system is configured to expand said bone replacement in response to a force exerted by said anchoring member due to the growth of the second bone portion; and
a bearing component that is configured to engage said bone replacement and adapted to secure to the second bone portion.

8. The device of claim 7, wherein said bearing component further includes a cannulated portion through which the connection system passes.

9. The device of claim 8, wherein said bearing component is a tibial resurfacing component.

10. A non-invasive expandable bone device adapted to be in a first bone portion of a patient that is capable of using growth of a second bone portion to elongate the first bone portion, the device comprising:
a bone replacement configured to be secured to the first bone portion;
an anchoring member configured to be secured to the second bone portion; and
a connection system configured to connect said bone replacement to said anchoring member,
wherein said connection system is configured to expand said replacement section in response to the growth of the second bone portion, and
wherein said connection system includes a cable that connects said bone replacement to said anchoring member and transmits a force from said anchoring member to said bone replacement to expand said bone replacement.

11. A non-invasive expandable bone device adapted to be in a first bone portion of a patient that is capable of using growth of a second bone portion to elongate the first bone portion, the device comprising:
a bone replacement section having a housing, an expansion shaft, a connection system and an implant member; and
an anchoring member secured to the second bone portion and spaced from said implant member,
wherein said expansion shaft is configured to translate within said housing a first distance and is adapted to connect to the first bone portion, said first distance between said housing and the first bone member,
wherein said implant member is configured to be secured to at least a portion of the second bone portion and includes a cannulated portion through which said connection system passes,
wherein growth of the second bone portion causes an increase of a second distance between said implant portion and said anchoring member, said increase of said second distance causes said anchoring member to exert a force on said connection system causing an increase of said first distance,
wherein said connection system includes a flexible connector secured to said anchoring member and connected to said expansion shaft,
wherein movement of said anchoring member causes movement of said expansion shaft and
wherein said bone replacement section further includes an articulable joint.

12. The bone device of claim 11, wherein said cable includes a plurality of projections that meshingly engage said expansion shaft.

13. The bone device of claim 11, wherein said connection system includes an anti-collapse device.

14. The bone device of claim 11, wherein the anchoring member includes an anchor plug that is fixedly secured to an intramedullary canal of the second bone portion with at least one of mechanical threads, bonding, mechanical fasteners, and combinations thereof.

15. The bone device of claim 11 further comprising an intramedullary stem capable of being secured to the first bone portion.

16. The bone device of claim 15, wherein said expansion shaft is configured to releaseably connect to said intramedullary stem.

17. The bone device of claim 15, wherein said intramedullary stem is modular and adapted to fit variable sizes of an intramedullary canal.

18. The bone device of claim 11, wherein said first bone portion is a femur and the second bone portion is a tibia.

19. The implant of claim 18, wherein the housing comprises a distal femoral replacement.

20. The implant of claim 18, wherein the anchoring member is configured to be secured to a tibial intramedullary canal.

21. The implant of claim 18, wherein the second bone implant is configured to be a resurfacing tibial component.

22. The implant of claim 11, wherein said housing includes a distal femoral replacement and said bone implant includes a resurfacing tibial component.

23. The implant of claim 22, wherein said articulable joint includes a cannulated portion through which the connection system passes.

24. The implant of claim 23, wherein said cannulated portion is configured to prevent tension of said connection system by flexion and extension of said articulable joint.

25. A non-invasive expandable bone device adapted to be in a first bone portion of a patient that is capable of using growth of a second bone portion to elongate the first bone portion, the device comprising:
a bone replacement section having a cannulated articulable joint member connecting the first bone portion to the second bone portion,
an anchoring member configured to be secured to the second bone portion; and
a connection system including a flexible connector that connects said bone replacement to said anchoring member,
wherein said connection system is configured to expand said bone replacement section in response to a force exerted by said anchoring member due to the growth of the second bone portion; and
wherein said articulable cannulated joint is configured to prevent additional application of tension on said connection system by the said articulable cannulated joint.

26. A non-invasive expandable bone device adapted to be in a first bone portion of a patient that is capable of using growth of a second bone portion to elongate the first bone portion, the device comprising:
a bone replacement section having a housing, an expansion shaft, a connection system and an implant member;
an anchoring member capable of being secured to the second bone portion and spaced from said implant member; and
an intramedullary stem capable of being secured to the first bone portion,
wherein said expansion shaft is configured to translate within said housing a first distance and is adapted to connect to the first bone portion, said first distance is between said housing and the first bone member, wherein said implant member is configured to be secured to at least a portion of the second bone portion and includes a cannulated portion through which said connection system passes, wherein growth of the second bone portion causes an increase of a second distance between said implant member and said anchoring member, said increase of said second distance causes said anchoring member to exert a force on said connection system causing an increase of said first distance, wherein said connection system includes a cable secured to said anchoring member and connected to said expansion shaft, and wherein movement of said anchoring member causes movement of said expansion shaft.

27. The bone device of claim 26, wherein said expansion shaft is configured to releaseably connect to said intramedullary stem.

28. The bone device of claim 26, wherein said intramedullary stem is modular and adapted to fit variable sizes of an intramedullary canal.

* * * * *